United States Patent [19]

Sivak et al.

[11] Patent Number: 4,865,985
[45] Date of Patent: Sep. 12, 1989

[54] CONTAINERS FOR CULTURING AND TESTING OF VERTEBRATE LENSES

[75] Inventors: Jacob G. Sivak, Waterloo, Canada; Ahuva Dovrat, Torrance, Calif.; David Gershon, Tivon, Israel

[73] Assignee: Canadian Industrial Innovation Centre Waterloo, Waterloo, Canada

[21] Appl. No.: 844,579

[22] Filed: Mar. 27, 1986

[30] Foreign Application Priority Data

Apr. 17, 1985 [CA] Canada .................................. 479406

[51] Int. Cl.$^4$ ............................................. C12M 3/00
[52] U.S. Cl. .................................... 435/284; 435/285; 435/287; 435/297; 435/298; 435/299; 435/300; 435/301; 422/102
[58] Field of Search ................ 435/287, 283, 284, 285, 435/297, 298, 299, 300, 301; 422/102

[56] References Cited

U.S. PATENT DOCUMENTS

| | | | |
|---|---|---|---|
| 2,942,520 | 6/1960 | Rose | 435/284 X |
| 3,128,902 | 4/1964 | Barnum | 435/284 X |
| 4,308,351 | 12/1981 | Leighton et al. | 435/284 |
| 4,358,425 | 11/1982 | Finney et al. | 422/102 |
| 4,435,508 | 3/1984 | Gabridge | 435/284 |
| 4,446,234 | 5/1984 | Russo et al. | 435/284 X |
| 4,652,429 | 3/1987 | Konrad | 422/102 |
| 4,668,633 | 5/1987 | Walton | 435/298 |

FOREIGN PATENT DOCUMENTS

| | | | |
|---|---|---|---|
| 0239697 | 10/1987 | European Pat. Off. | 435/284 |
| 0901266 | 1/1982 | U.S.S.R. | 435/284 |

OTHER PUBLICATIONS

"Spherical Aberration of the Crystalline Lens" J. G. Sivak and R. O. Kreuzer, Vision Res. vol. 23, pp. 59–70, 1983.

"Aging and the Optical Quality of the Rat Crystalline Lens" J. G. Sivak and A. Dovrat, Investigative Opthalmology & Visual Science, vol. 24, pp. 1162–1166, Sep. 1983.

Primary Examiner—Barry S. Richman
Assistant Examiner—Lynn M. Kummert
Attorney, Agent, or Firm—R. Craig Armstrong

[57] ABSTRACT

A container for holding and culturing a lens is disclosed, comprising a transparent base member, a transparent lens carrier supported laterally in the base member and having a central aperture, and a transparent cover engaging the base member for enclosing the lens carrier within the container. The base is circular in top view, and in sectional elevation is in the form of a flanged U-shape, forming a well. The lens carrier is a circular plate with a central aperture. The lip of the aperture tapers downwardly in order to support the outer rim of the lens to be tested. The cover has an annular flange and a raised center section with angled sidewalls. The sidewalls have two flat sections offset from each other by 90 degrees, which act as viewing ports. The lens to be studied is centered in the aperture in the bottom of the lens carrier. The lens carrier is ordinarily provided with passage holes to permit the free passage of the culture medium from one side of the lens to the other. However, a lens carrier without such holes may be used if it is desired to expose the anterior and posterior lens surfaces to separate media.

12 Claims, 1 Drawing Sheet

CONTAINERS FOR CULTURING AND TESTING OF VERTEBRATE LENSES

This invention relates to containers for holding and culturing lenses, especially for purposes such as the evaluation of focal length changes using apparatus as described in a co-pending United States patent application entitled "Method and Apparatus for In Vitro Evaluation of Focal Length and Focal Length Changes in Lenses from Human and Animal Eyes", Ser. No. 844,944, filed contemporaneously with the present application.

The lens of the eye has been the centre of intense recent attention, both because of possible benefits related to understanding the causes and means of preventing cataracts and because the continued growth of the lens through life makes it an ideal tissue for the study of aging. The fact that it is avascular and that it is encapsulated inside the eye within an acellular envelope has somewhat simplified handling and maintenance, and has prompted numerous efforts to culture the intact lens.

Since the lens is an optical device as well as being a biological tissue it is reasonable to expect that the measurement of lens optical quality would be a primary means of monitoring lens function during culture and cataractogenesis research. However, effects to use the optical properties of the lens as a measure of lens condition have been desultory and largely qualitative in nature. Direct photography of the lens has been the most common approach. In some instances a grid has been photographed through the lens and one group of researchers has developed a shadowgram index of lens transparency. One group has determined lens turbidity by measuring the intensity of a helium-neon laser beam as it passed through various portions of the lens.

Such efforts in the prior art indicate that the main optical interest has been in the detection of obvious cataractous changes in lens transparency. However, it is known that the physical parameters of the lens are sensitive to factors known to affect single cells, and that changes in lens biochemistry begin well before the appearance of pronounced opacities. Variations in refractive state of the eye, presumably due to change in lens volume and curvature, are among the early indications of diabetes mellitus while the additon of a variety of materials (including glucose and xylose) to lens culture media affects lens weight and water content.

A method has now been developed for examining and evaluating changes in lens focal length, as described in the above-mentioned copending application, involving the projection of fine laser beams through lenses maintained in vitro and photographing the focal effects for the analysis of lens aberrations. By varying beam separation and laser color, spherical and chromatic aberration can be analyzed. The method has been used to demonstrate the imprecise refractive quality of the aged human lens, presumably due to variations in refractive index associated with age-related protein aggregation. It has also been used to determine the effect of the age on spherical aberration of the rat lens. Apparatus has been developed to permit the use of the method to monitor lens refractive condition during lens culture experiments, as described in the copending application.

In order to carry out the method, it is necessary to have some means for suitably holding the lens for culturing and for examination and testing, and it is to this need that the present invention is addressed.

The present container is particularly useful in conjunction with the method and apparatus of the copending application. This apparatus may be described briefly as follows.

Suspended above the base of a cabinet by a carousel support assembly is a carousel plate having a number of spaced holes capable of receiving lens containers. A carousel drive servo motor rotates the carousel from lens container position to lens container position. Also mounted on the cabinet base, beneath the carousel, is an X-Y table assembly with a table on which a helium-neon laser is mounted. The laser is horizontally mounted, but has a prism assembly attached at its output, so that the laser beam is deflected upwardly. By appropriate positioning of the X-Y table and the lens containers in the carousel holes, the laser beam may be projected up through a lens held in a lens container.

Also installed in the cabinet, above the carousel, is a horizontally oriented video camera. Mirrors are mounted within the cabinet in order to provide the video camera with two views of the lens focal point area within the lens container being examined, the viewpoints being offset from each other by 90 degrees. The video camera signal is fed to a personal computer for analysis. A display monitor and printer are connected to the computer. The software may be directed to display and print the actual video camera image, or to digitize the information and produce a display or printout illustrating the spherical aberration of the lens, in the form of a graph showing the variation in back vertex power.

It is an object of the present invention to provide a container suitable for holding and culturing a lens, useful for purposes such as the examination and evaluation of lens focal length changes using the apparatus described in the copending application.

Thus in accordance with the present invention there is provided a container for holding and culturing a lens, comprising a transparent base member, a transparent lens carrier supported laterally in the base member and having a central aperture, and a transparent cover engaging the base member for enclosing the lens carrier within the container.

Further features of the invention will be described or will become apparent in the course of the following detailed description.

In order that the invention may be more clearly understood, the preferred embodiment thereof will now be described in detail by way of example, with reference to the accompanying drawings, in which.

In the preferred embodiment of the present invention, each of the containers 1 designed to contain a lens consists of a base 2, a lens carrier 3, and a cover 4. The base, lens carrier and cover are all of transparent material such as glass or a transparent plastic (e.g. acrylic or styrene).

Figure 6:
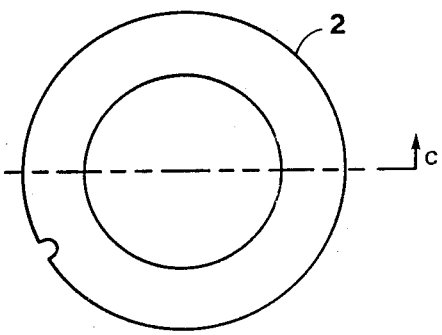
FIG. 6 is a top view of the base.
Figure 7:
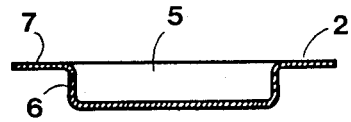
FIG. 7 is a sectional elevation view of the base, at section C—C in FIG. 6.

The base 2, illustrated in FIGS. 6 and 7, is circular in top view, and in sectional elevation is in the form of a flanged U-shape. The central depression forms a well 5 having a cylindrical wall 6, which may be used for positioning the container in a hole in a carousel of containers for testing. The annular flange 7 then supports the container above the carousel, with the well protruding downwardly into the hole in the carousel and the wall of the well contacting the sidewall of the hole.

Figure 4:
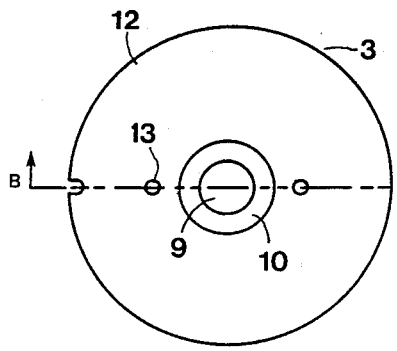
FIG. 4 is a top view of the lens carrier.
Figure 5:
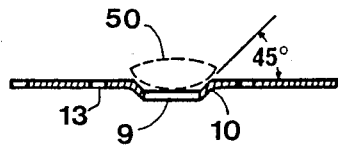
FIG. 5 is a sectional elevation view of the lens carrier, at section B—B in FIG. 4.

The lens carrier 3, shown in FIGS. 4 and 5, is essentially a circular plate with a central aperture 9. The lip 10 of the aperture tapers downwardly, at an angle of 45 degrees for example, in order to support the outer rim of the lens to be tested. The region of the plate near the periphery constitutes an annular flange 12.

Figure 1:
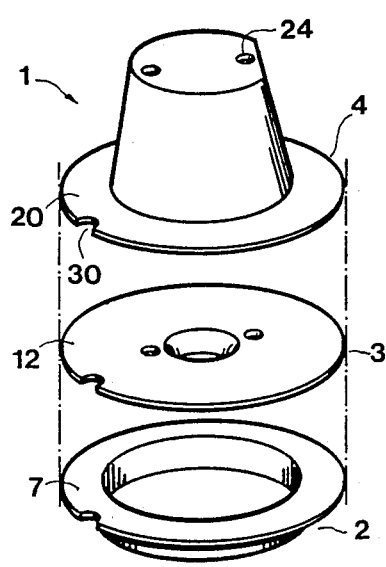
FIG. 1 is an exploded oblique view of the preferred embodiment of the container, comprising a cover, a lens carrier, and a base.
Figure 2:
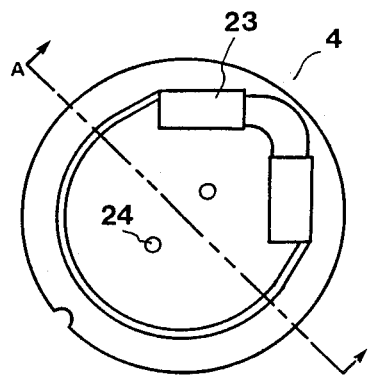
FIG. 2 is a top view of the cover.
Figure 3:
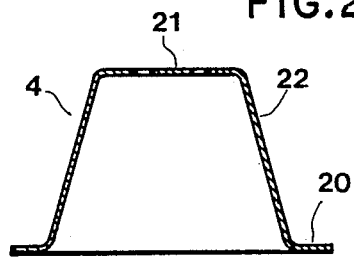
FIG. 3 is a sectional elevation view of the cover, at section A—A in FIG. 2.

The cover 4, shown in FIGS. 1 and 2, has an annular flange 20, and a raised centre section 21 with angled sidewalls 22 connecting the annular flange to the centre section. The sidewalls are not perfectly conical, but rather have two flat sections 23 offset from each other by 90 degrees, which act as viewing ports in the apparatus described in the copending application, the purpose of the flat sections being to minimize distortion. The cover preferably extends away from the lens carrier by at least about one inch, so that the lens focal points of most vertebrate lens are well within the container dimensions.

The base, lens carrier and cover annular flanges 7, 12 and 20 respectively, are of substantially the same diameter, namely about 3.25 inches, and rest in turn on each other and are sealed to each other by any suitable means such as ultrasonic welding or adhesive.

Each annular flange 7, 12 and 20 is provided with a small notch 30 at its periphery, which may be used to position the container properly in the carousel hole, especially if the carousel is provided with a pin near the edge of the hole to engage in the notches.

The lens 50 to be studied is centered in the aperture 9 in the bottom of the lens carrier 3. The selected diameter of the aperture depends of course on the type of lens to be examined, and would ordinarily range from about 2.5 millimeters for rat lenses to up to about 13 millimeters for cow lenses, for example.

Lens organ culture is usually carried out by immersing the entire lens in a single culture medium. However, the container of the present invention has been designed so that the anterior and posterior lens surfaces may be exposed to separate media, one contained between the base and the lens carrier element, and the other contained between the cover and the lens carrier element. So that this may be accomplished, the rim of the lens can be glued to the lip 10 of the aperture with silicone adhesive such as SYLGARD R (Trademark of Dow Corning Corp.). The maintenance of an effective separation between the lens surfaces can be confirmed by the observation of steady asymmetry in electrical potential (usually 22 to 26 mV) when electrodes are placed in the separate media regions with an experimental lens in place, using the technique decribed by Duncan et al, (1977) "A simple chamber for measuring lens assymetry potentials", Exp. Eye Res. 25, 391-398.

Thus it is possible to compare the effect of using a single medium (M199 with Earle's salts and 5% fetal calf serum, for example) to, for example, a situation in which the anterior lens is bathed in M199 while the posterior surface is in contact with a vitreous medium.

This ability to contact the anterior and posterior sides of the lens with different media is useful not only for the simulation of real conditions, but also and particularly for such uses as subjecting one side of the lens to a toxic substance to observe the effect.

For lenses cultured in the containers, medium pH is preferably maintained at about 7.4 with bicarbonate buffering while the incubator temperature is preferably kept at around 35 degrees Celsius.

It should be noted at this point that the centre section 21 of the cover 4 is provided with two small holes 24, which are fitted with conventional rubber seals for hypodermic injection of culturing medium.

The lens carrier 3 is ordinarily provided with passage holes 13 to permit the free passage of culture medium from one side of the lens to the other. However, if it is desired to have different media on opposite sides of the lens, a lens carrier without such holes must be used. In that case, a small rubber hypodermic port must be provided in the base (not illustrated) so that the culture medium may be injected into the area between the lens carrier and the base.

The cover is preferably provided with a small textured area or other means (not illustrated) on which lens information may be written for identification purposes.

It will be appreciated that the above description relates to the preferred embodiment by way of example only. Many variations on the invention will be obvious to those knowledgeable in the field, and such obvious variations are within the scope of the invention as described and claimed, whether or not expressly described.

The preferred embodiment, with its viewing ports, is intended particularly for use with the apparatus and method described in the above-mentioned copending application. However, it should be clearly understood that obvious variations could be used for other applications. In other applications, for example, viewing ports such as those described might not be required, or might be differently configured or located elsewhere in the structure of the container.

Furthermore, it should be obvious that the container need not be round. It could just as easily be square, for example, as indeed it was in an early experimental embodiment. The round shape was selected as the preferred embodiment merely to facilitate manufacture through a vacuum moulding process.

Also, the lens carrier need not be sealed between the base and the cover, as long as separate media were not desired in the upper and lower chambers. The lens carrier could be simply supported by the base, for example. It should also be evident that even in the case where the upper and lower chambers were to be kept separate, the lens carrier could be suitably sealed to the base or to the cover, and not necessarily between both as in the case of the preferred embodiment. The lens carrier could be sealed to the base alone, for example, as long as the base and the cover were themselves sealed to each other.

Furthermore, the base and cover need not necessarily be actually sealed to each other. It is sufficient, for example, in some embodiments, to have a cover which merely fits over and rests on the base, provided that adequate sterility can be maintained.

The embodiments of the invention in which an exclusive property or privilege is claimed are defined as follows:

1. A container for holding and culturing a lens, comprising a transparent base member, a transparent lens carrier supported laterally in said base member and having means defining a central lens-supporting aperture, and a transparent cover engaging said base member for enclosing said lens carrier within said container, with no structural elements located between said transparent base member and said transparent cover so as to attentuate or block the passage of light through said base member, said aperture and said cover.

2. A container as recited in claim 1, in which said said cover extends away from said lens carrier by at least about one inch.

3. A container as recited in claim 1, further comprising at least one rubber-membrane injection port provided in said cover for sealingly injecting culture medium into said container.

4. A container as recited in claim 3, in which said cover extends away from said lens carrier by at least about one inch.

5. A container as recited in claim 1, in which an outer periphery of said lens carrier is sealed to said base member, whereby upper and lower chambers are defined respectively between said lens carrier and said cover and said lens carrier and said base, and whereby said chambers may be kept separate from each other by sealingly bonding a lens to a margin of said aperture.

6. A container as recited in claim 5, in which said cover extends away from said lens carrier by at least about one inch.

7. A container as recited in claim 5, further comprising at least one rubber-membrane injection port provided in said cover for sealingly injecting culture medium into said upper chamber and at least one rubber-membrane injection port provided in said base for sealingly injecting culture medium into said lower chamber.

8. A container as recited in claim 7, in which said cover extends away from said lens carrier by at least about one inch.

9. A container as recited in claim 5, in which said lens carrier is provided with means defining at least one aperture apart from said central aperture, whereby culture medium in said container may flow between said upper and lower chambers.

10. A container as recited in claim 9, in which said cover extends away from said lens carrier by at least about one inch.

11. A container as recited in claim 9, further comprising at least one rubber-membrane injection port provided in said cover for sealingly injecting culture medium into said container.

12. A container as recited in claim 11, in which said cover extends away from said lens carrier by at least about one inch.

* * * * *